(12) United States Patent
Chang et al.

(10) Patent No.: US 6,979,738 B2
(45) Date of Patent: Dec. 27, 2005

(54) QUADRUPLEX STABILIZER

(75) Inventors: Ta-Chau Chang, Taipei (TW);
Cheng-Chung Chang, Taipei (TW);
Jin-Yi Wu, Chiayi (TW)

(73) Assignee: Academia Sinica, Taipei (TW)

( * ) Notice: Subject to any disclaimer, the term of this patent is extended or adjusted under 35 U.S.C. 154(b) by 113 days.

(21) Appl. No.: 10/690,984

(22) Filed: Oct. 22, 2003

(65) Prior Publication Data

US 2005/0090671 A1 Apr. 28, 2005

(51) Int. Cl.[7] ............... C07D 401/14; A61K 31/4439; A61K 31/501
(52) U.S. Cl. .................. 544/357; 546/256; 435/6
(58) Field of Search .................. 544/357; 546/256; 435/6

(56) References Cited

U.S. PATENT DOCUMENTS 6,156,763 A * 12/2000 Kerwin et al. .............. 514/279

FOREIGN PATENT DOCUMENTS

JP 2002-172864 * 6/2002

OTHER PUBLICATIONS

Arthanari et al. "Fluorescent Dyes Specific for Quadruplex DNA", Nucleic Acids Research, 26(16), 3724-3728, 1998.*
Duan et al., Chemical Abstracts, 134:107619, 2000.*
Krieg et al., Chemical Abstract, 134:159233, 2000.*
Duan et al., Materials Research Society Symposium Proceedings, 598, BB3.31.1-BB3.31.6, 2000.*

Chang et al., "a Carbazole Derivative Synthesis for Stabilizing the Quadruplex Structure", Journal of the Chinese Chemical Society 50:185-188, 2003.
Chang et al., "A Fluorescent Carbazole Derivative: High Sensitivity for Quadruplex DNA", Anal. Chem. 75:6177-6183, 2003.

* cited by examiner

Primary Examiner—Fiona T. Powers
(74) Attorney, Agent, or Firm—Fish & Richardson P.C.

(57) ABSTRACT

This invention relates to carbazole compounds of the following formula:

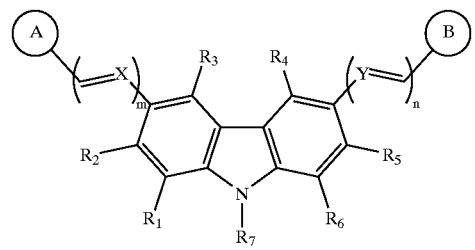

In the above formula, each of rings A and B, independently, is heteroaryl containing at least one nitrogen atom; each of X and Y, independently, is CH or N; each of $R_1$–$R_6$, independently, is H, $C_1$–$C_8$ alkyl, $C_2$–$C_8$ alkenyl, $C_2$–$C_8$ alkynyl, $C_3$–$C_8$ cycloalkyl, $C_3$–$C_8$ heterocycloalkyl, aryl, heteroaryl, OH, $C_1$–$C_6$ alkoxy, aryloxy, heteroaryloxy, $NH_2$, $C_1$–$C_6$ alkylamino, $C_1$–$C_{12}$ dialkylamino, arylamino, diarylamino, or halogen; $R_7$ is H, $C_1$–$C_8$ alkyl, $C_2$–$C_8$ alkenyl, $C_2$–$C_8$ alkynyl, $C_3$–$C_8$ cycloalkyl, $C_3$–$C_8$ heterocycloalkyl, aryl, heteroaryl; and <each of m and n, independently, is 1, 2, or 3.

22 Claims, No Drawings

QUADRUPLEX STABILIZER

BACKGROUND

Telomeres, the ends of chromosomes, are essential for the stability and replication of eukaryotic chromosomes. See, e.g., Williamson J. R., *Annu. Rev. Biophys. Biomol. Struct.*, 1994, 23:703. Telomeric sequences are shortened during cell division since DNA synthesis cannot fully replicate the extreme ends of chromosomes. A reduction in the telomere length to a critical level can lead to genomic instability, aberrant chromosome fusion, and cellular senescence. See, e.g., Harley et al., *Curr. Opin. Genet. Dev.*, 1995, 5:249. In contrast, telomeres of tumor cells do not shorten during cell replication due to the presence of a telomerase, which allows adding nucleotides to telomeric DNA at the ends of chromosomes. See, e.g., Feng et al., *Science*, 1995, 269:1236. Telomerase is expressed in more than 85% of tumor cells, but not in most somatic cells. See Harley et al., *Nature*, 1990, 345:458. Thus, telomerase is becoming a promising target for cancer diagnosis and chemotherapy. See Blackburn E. H., *Nature*, 1991, 350:569.

Telomeres generally consist of many tandem repeats of guanine-rich (G-rich) motifs, such as $T_2AG_3$ in human telomeres. See Morin G B., *Cell*, 1989, 59:521. It is shown in in vitro assays that the 3'-overhang G-rich single strand adopts an intramolecular G-quadruplex structure. The quadruplex structure is stabilized by π—π interaction of a cyclic G-quartet, formed through Hoogsteen hydrogen bonding. See Gellert et al., *Proc. Natl. Acad. Sci. USA*, 1962, 48:2013. Since folding telomeric DNA into G-quadruplexes has been shown to inhibit telomerase activities in vitro, G-quadruplexes have also been considered as potential targets for antitumor agents. See Zahler et al., *Nature*, 1991, 350:718.

SUMMARY

This invention is based on the unexpected discovery that certain carbazole compounds can thermally stabilize G-quadruplexes of human telomeres.

In one aspect, this invention features carbazole compounds of the following formula:

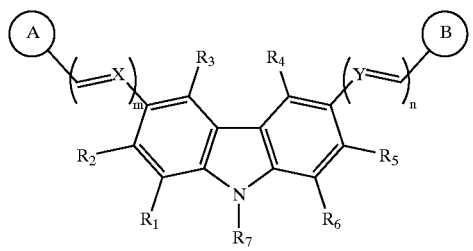

In the above formula, each of rings A and B, independently, is heteroaryl containing at least one nitrogen atom; each of X and Y, independently, is CH or N; each of $R_1$–$R_6$, independently, is H, $C_1$–$C_8$ alkyl, $C_2$–$C_8$ alkenyl, $C_2$–$C_8$ alkynyl, $C_3$–$C_8$ cycloalkyl, $C_3$–$C_8$ heterocycloalkyl, aryl, heteroaryl, OH, $C_1$–$C_6$ alkoxy, aryloxy, heteroaryloxy, $NH_2$, $C_1$–$C_6$ alkylamino, $C_1$–$C_{12}$ dialkylamino, arylamino, diarylamino, or halogen; $R_7$ is H, $C_1$–$C_8$ alkyl, $C_2$–$C_8$ alkenyl, $C_2$–$C_8$ alkynyl, $C_3$–$C_8$ cycloalkyl, $C_3$–$C_8$ heterocycloalkyl, aryl, heteroaryl; and each of m and n, independently, is 1, 2, or 3.

A subset of the above-described carbazole compounds features that each of rings A and B is heteroaryl containing one or two nitrogen atoms. In these compounds, each of m and n is 1; each of $R_1$–$R_7$ is H; and each of X and Y is CH or N.

The term "alkyl" refers to a saturated, linear or branched hydrocarbon moiety, such as $CH_3$, —$CH_2$—, or branched $C_3H_7$. The term "alkenyl" refers to a linear or branched, non-aromatic hydrocarbon moiety having at least one double bond, such as —CH=$CH_2$ or —CH=CH—. The term "alkynyl" refers to a linear or branched, non-aromatic hydrocarbon moiety having at least one triple bond, such as —C≡CH or —C≡C—. The term "cycloalkyl" refers to a saturated cyclic hydrocarbon moiety, such as cyclohexyl. The term "heterocycloalkyl" refers to a saturated cyclic moiety having at least one ring heteroatom, such as 4-tetrahydropyranyl. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "alkoxy" refers to a linear or branched, saturated or unsaturated, non-aromatic hydrocarbon moiety containing an oxygen radical, such as —$OCH_3$ or —OCH=$C_2H_5$. The term "aryloxy" refers to a moiety having at least one aromatic ring and an oxygen radical bonded to the aromatic ring, such as phenoxy. The term "heteroaryloxy" refers to a moiety having at least one aromatic ring that contains at least one ring heteroatom and an oxygen radical bonded to the aromatic ring, such as 4-pyrindinoxy.

Alkyl, alkenyl, alkynyl, cycloalkyl, heterocycloalkyl, aryl, heteroaryl, alkoxy, aryloxy, heteroaryloxy, alkylamino, dialkylamino, arylamino, and diarylamino mentioned herein include both substituted and unsubstituted moieties. Possible substituents on cycloalkyl, heterocycloalkyl, aryl, heteroaryl, aryloxy, heteroaryloxy, arylamino, and diarylamino include $C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_1$–$C_{10}$ alkoxy, aryl, aryloxy, heteroaryl, heteroaryloxy, amino, $C_1$–$C_{10}$ alkylamino, $C_1$–$C_{20}$ dialkylamino, arylamino, diarylamino, hydroxyl, halogen, thio, $C_1$–$C_{10}$ alkylthio, arylthio, $C_1$–$C_{10}$ alkylsulfonyl, arylsulfonyl, cyano, nitro, acyl, acyloxy, carboxyl, and carboxylic ester. On the other hand, possible substituents on alkyl, alkenyl, alkynyl, alkoxy, alkylamino, and dialkylamino include all of the above-recited substituents except $C_1$–$C_{10}$ alkyl, $C_2$–$C_{10}$ alkenyl, and $C_2$–$C_{10}$ alkynyl. Cycloalkyl and heterocycloalkyl can also be fused with aryl or heteroaryl.

The carbazole compounds described above include the compounds themselves, as well as their salts and their prodrugs, if applicable. A salt, for example, can be formed between an anion and a positively charged group (e.g., ammonium) on a carbazole compound. Suitable anions include chloride, bromide, iodide, sulfate, sulfite, perchlorate, hexafluorophosphate, nitrate, phosphate, citrate, methanesulfonate, trifluoroacetate, and acetate. Likewise, a salt can also be formed between a cation and a negatively charged group (e.g., carboxylate) on a carbazole compound. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active carbazole compounds.

In another aspect, this invention features a method for stabilizing a G-quadruplex of a human telomere or a telomere of other mammals. The method includes contacting a telomere with a carbazole compound of the same formula shown above. This method can be used to treat any telomerase-related diseases in which inhibiting telomerase activities is desired. In addition, this method can be used for in vitro assays (e.g., identifying a G-quadruplex of a telomere) or in vivo animal model testing or screening the efficacy of a carbazole compound mentioned above as a drug for treating telomerase-related diseases (e.g., cancer). "Treating" mentioned herein refers to administering one or more carbazole compounds in an effective amount to a subject, who has an telomerase-related disease, a symptom of such a disease, or a predisposition toward such a disease, with the purpose to confer a therapeutic effect, e.g., to cure, relieve, alter, affect, ameliorate, or prevent the telomerase-related disease, the symptom of it, or the predisposition toward it. "An effective amount" mentioned herein refers to the amount of one or more carbazole compounds described above that is required to confer a therapeutic effect on a treated subject.

In addition, this invention encompasses a pharmaceutical composition that contains an effective amount of at least one of the above-mentioned carbazole compounds and a pharmaceutically acceptable carrier.

Also within the scope of this invention is a composition containing one or more of the carbazole compounds described above for use in treating a telomerase-related disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are exemplary carbazole compounds, compounds 1–8, of this invention.

Compound 1
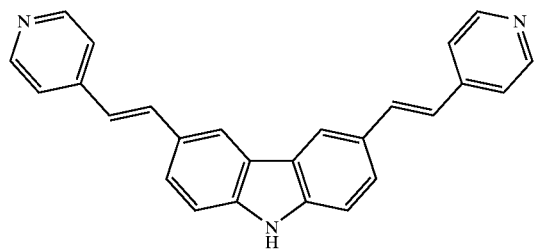

Compound 2
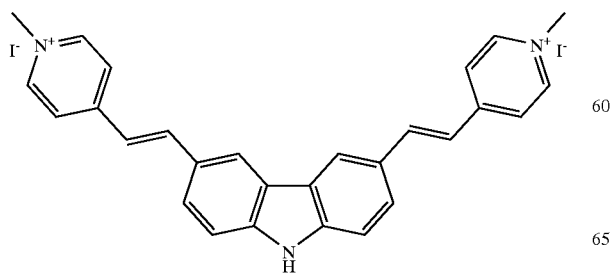

-continued

Compound 3
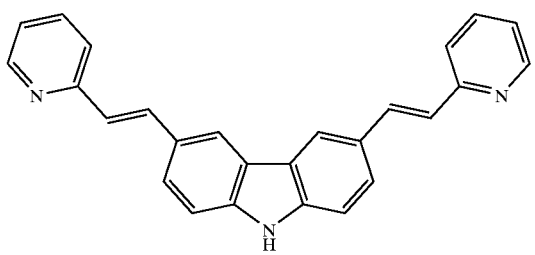

Compound 4
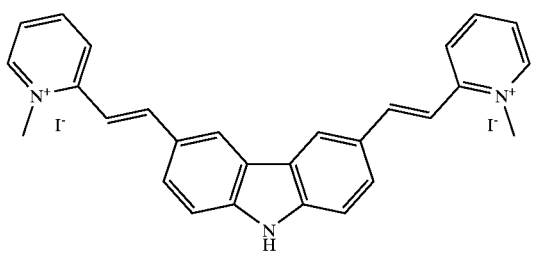

Compound 5
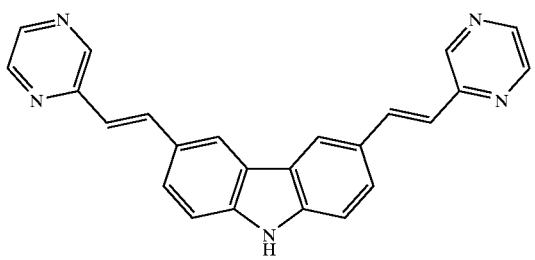

Compound 6
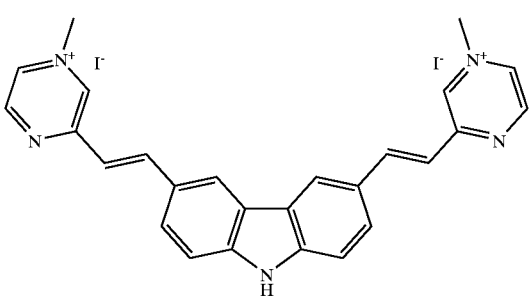

Compound 7
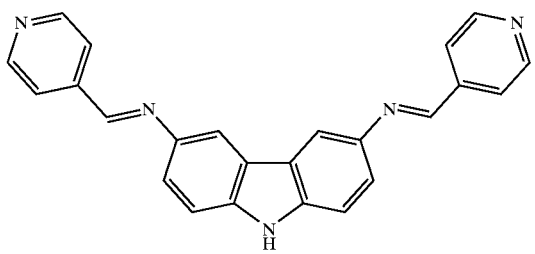

-continued

Compound 8

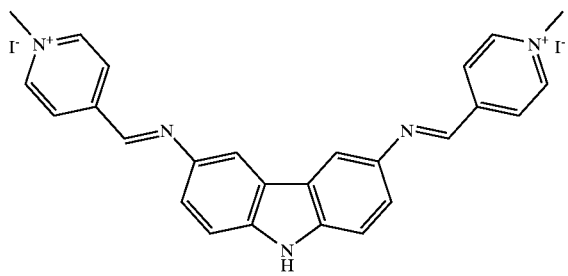

The carbazole compounds described above can be prepared by methods well known in the art, as well as by the synthetic routes disclosed herein. For example, one can react 3,6-dibromocarbazole with an olefin containing a heteroaryl group with at least one nitrogen atom in the presence of a palladium catalyst to produce an intermediate, 3,6-bis(heteroaryl-vinyl)carbazole. The intermediate can then be treated with methyl iodide to produce a corresponding iodide salt. As another example, one can react 3,6-diaminocarbazole with a formaldehyde containing a heteroaryl group with at least one nitrogen atom to produce an intermediate, 3,6-bis(heteroaryl-methylidene-imino)-carbazole. Similarly, this intermediate can also be converted to a corresponding iodide salt upon treating with methyl iodide.

Shown below is a scheme that depicts the synthesis of compounds 1–8 mentioned above.

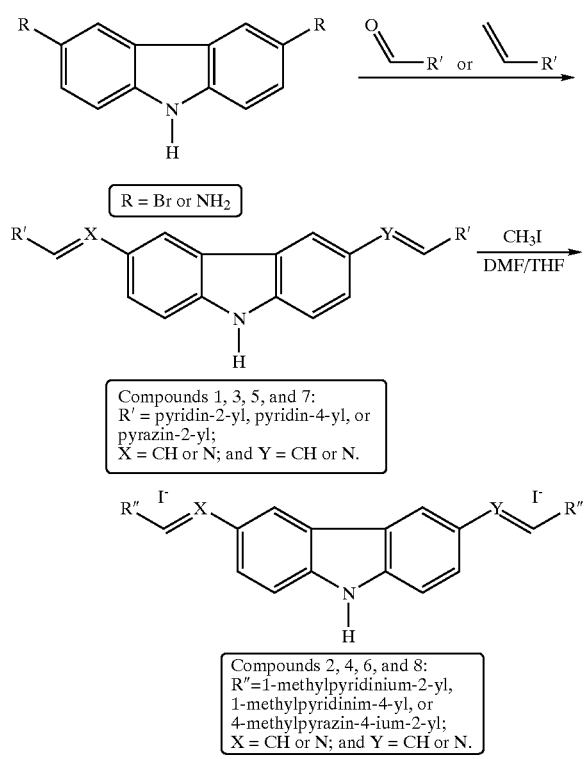

Details of synthesis of compounds 1–8 are described in Examples 1–8, respectively. To prepare other carbazole compounds, pyridinyl or pyrazinyl shown in the above scheme can be replaced by another heteroaryl containing at least one nitrogen atom (e.g., pyrrolyl, imidazolyl, pyrimidinyl, or indolyl).

The chemicals used in the above-described synthetic route may include, for example, solvents, reagents, catalysts, protecting group reagents, and deprotecting group reagents. The methods described above may additionally include steps, either before or after the steps described specifically herein, to add or remove suitable protecting groups in order to ultimately allow synthesis of a carbazole compound. In addition, various synthetic steps may be performed in an alternate sequence or order to give the desired carbazole compounds. Synthetic chemistry transformations and protecting group methodologies (protection and deprotection) useful in synthesizing applicable carbazole compounds are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A carbazole compound thus synthesized can be further purified by a method such as column chromatography, high-pressure liquid chromatography, or recrystallization.

Note that the carbazole compounds contain at least two double bonds, and may further contain one or more asymmetric centers. Thus, they can occur as racemates and racemic mixtures, single enantiomers, individual diastereomers, diastereomeric mixtures, and cis- or trans- or E- or Z-double bond isomeric forms. All such isomeric forms are contemplated.

Also within the scope of this invention is a pharmaceutical composition contains an effective amount of at least one carbazole compound described above and a pharmaceutical acceptable carrier. Further, this invention covers a method for stabilizing a G-quadruplex of a human telomere or a telomere of other mammals. This method can be used to treat a subject with telomerase-related diseases by administering to it an effective amount of one or more of carbazole compounds. Such a subject can be identified by a health care professional based on results from any suitable diagnostic method.

When using the method of this invention to treat a subject with telomerase-related disease, one can determine effective doses by methods well known in the art. For example, the interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the carbazole compounds can range from about 0.1 mg/Kg to about 100 mg/Kg. Effective doses will vary, as recognized by those skilled in the art, depending on, e.g., the types of diseases treated, route of administration, excipient usage, and the possibility of co-usage with other therapeutic treatment.

To treat a telomerase-related disease, a composition having one or more of the above-mentioned compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, intraperitoneal, intratracheal or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow # 10.

The carbazole compounds of this invention can be preliminarily screened for their efficacy in stabilizing G-quadruplexes by in vitro assays (See Example 9 below). Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compound 1:
3,6-Bis-(2-pyridin-4-yl-vinyl)-9H-carbazole

Compound 1 was prepared following the procedures described below:

3,6-Dibromocarbazole (1.63 g, 5 mmol, Aldrich) was added into a high pressure flask containing a mixture of palladium(II) acetate (15 mg, Strem) and tri-o-tolyl phosphine (150 mg, Aldrich). To this flask was added a mixed solvent (triethylamine 5 mL/acetonitrile 15 mL) and 4-vinylpyridine (2 g, 20 mmol, Merck). The flask was sealed after bubbling nitrogen for 10 minutes. After keeping the reaction at ~105° C. for three days, precipitate was collected and then washed with $H_2O/CH_2Cl_2$ twice. The resultant insoluble solid was filtered and dissolved in THF, then dried over anhydrous $MgSO_4$. Compound 1 was collected as a yellow powder by filtration after recrystallization from THF filtrate (Yield: 62%, mp>300° C.).

$^1$H NMR (CD$_3$OD): δ 8.42 (d, J=5.7 Hz, 4H), 8.25 (s, 2H), 7.65 (d, J=8.4 Hz, 2H), 7.56 (d, J=16.2 Hz, 2H), 7.45 (d, J=5.7 Hz, 4H), 7.42 (d, J=8.4 Hz, 2H), 7.07 (d, J=16.2 Hz, 2H).

EA (373+1.5H$_2$O): calc (obs %) C, 83.64 (78.20), H, 5.09 (5.14), N, 11.26 (10.38).

EXAMPLE 2

Preparation of Compound 2: 3,6-bis-(2-(1-methylpyridinium-4-yl)-vinyl)-9H-carbazole diiodide Compound 2 was prepared following the procedures described below:

After refluxing 3,6-di(4-vinylpyridine) carbazole obtained in Example 1 with excess CH$_3$I in acetone, compound 2 was collected as an orange-red powder by filtration after recrystallization from methanol twice (Yield: 92%, mp>300° C.).

$^1$H NMR (DMSO-d$_6$): δ 8.77 (d, J=6.9 Hz, 4H), 8.59 (s, 2H), 8.19 (d, J=6.9 Hz, 4H), 8.20 (d, J=15.9 Hz, 2H), 7.90 (d, J=8.7 Hz, 2H), 7.64 (d, J=8.7 Hz, 2H), 7.53 (d, J=15.9 Hz, 2H).

EA (657+1.0H$_2$O): calc (obs %) C, 51.14 (49.87), H, 3.81 (4.03), N, 6.39 (6.32).

EXAMPLE 3

Preparation of Compound 3:
3,6-bis-(2-pyridin-2-yl-vinyl)-9H-carbazole

Compound 3 was prepared in a manner similar to that described in Example 1.

EXAMPLE 4

Preparation of Compound 4: 3,6-bis-(2-(1-methylpyridinium-2-yl)-vinyl)-9H-carbazole diiodide Compound 4 was prepared in a manner similar to that described in Example 2.

EXAMPLE 5

Preparation of Compound 5:
3,6-bis-(2-pyrazin-2-yl-vinyl)-9H-carbazole

Compound 5 was prepared in a manner similar to that described in Example 1.

EXAMPLE 6

Preparation of Compound 6: 3,6-bis-(2-(4-methylpyrazin-4-ium-2-yl)-vinyl)-9H-carbazole diiodide Compound 6 was prepared in a manner similar to that described in Example 2.

EXAMPLE 7

Preparation of Compound 7: N,N'-bis-(pyridin-4-ylmethylidene)-9H-carbazole-3,6-diamine Compound 7 was prepared in a manner similar to that described in Example 1.

EXAMPLE 8

Preparation of Compound 8: N,N'-bis-((1-methylpyridinium-4-yl)methylidene)-9H-carbazole-3,6-diamine diiodide Compound 8 was prepared in a manner similar to that described in Example 2.

EXAMPLE 9

Binding Between Carbazole Compounds and DNA Duplexes and Quadruplexes

Calf thymus (ct-DNA) and oligonucleotides AT, LD, GC, G10, LQ1, LQ2, LQ4, Tet12, Apt, Oxy12, Oxy28, Hum12, and Hum24 were purchased from Applied Biosystems. The sequences of these oligonucleotides are listed below:
AT: 5'-(AT)$_6$-3' (SEQ ID NO:1)
LD: 5'-GCGCA2T2GCGC-3' (SEQ ID NO:2)
GC: 5'-(GC)$_6$-3' (SEQ ID NO:3)
G10: 5'-d(G)$_{10}$-3' (SEQ ID NO:4)
LQ1: 5'-TG$_4$T-3' (SEQ ID NO:5)
LQ2: 5'-T$_2$G4T$_2$-3' (SEQ ID NO:6)
LQ4: 5'-T$_4$G$_4$-3' (SEQ ID NO:7)
Tet12: 5'-(T$_2$G$_4$)$_2$-3' (SEQ ID NO: 8)
Apt: 5'-G$_2$T$_2$G$_2$TGTG$_2$T$_2$G$_2$-3' (SEQ ID NO:9)
Oxy12: 5'-G$_4$T$_4$G$_4$-3' (SEQ ID NO:10)
Oxy28: 5'-G$_4$(T$_4$G$_4$)$_3$-3' (SEQ ID NO: 11)
Hum12: 5'-(T$_2$AG$_3$)$_2$-3' (SEQ ID NO:12)
Hum24: 5'-(T$_2$AG$_3$)$_4$-3' (SEQ ID NO:13)

Among them, ct-DNA and oligonucleotides AT, LD, and GC, can form duplexes, while oligonucleotides G10, LQ1, LQ2, LQ4, Tet12, Apt, Oxy12, Oxy28, Hum12, and Hum24 can form quadruplexes. For example, Apt can form a very stable unimolecular quadruplex with two G-quartets connected by one lateral TGT loop at one end and two parallel TT loops at the other end. Hum24 can form a unimolecular quadruplex with one diagonal T$_2$A-loop at one end and two parallel T$_2$A-loops at the other end of G-quartets. Tet12 and Hum12 can form a dimeric hairpin quadruplex with lateral loops. Oxy12 can form a dimeric hairpin quadruplex with a diagonal loop at each end of the quartets.

Absorption, Fluorescence, and circular Dihcroism (CD) Analysis of Carbazole Compounds and Their Complexes with DNA Duplexes and Quadruplexes Absorption Analysis Each oligonucleotide described above was mixed with a solution of 10 mM Tris-HCl (pH 7.5) and 150 mM NaCl and was denatured at 90° C. for 2 min. The mixture was then cooled slowly to room temperature and stored at 4° C. for more than 2 days before use. A test compound was then added to this solution to form a compound/DNA complex. The resultant complex was subjected to absorption analysis using a Hitachi U3200 UV-visible spectrophotometer.

The absorption spectra were taken for compound 2 and its complex with each oligonucleotide. The results showed that the absorption peak of compound 2 red shifted from 435 nm to ~450 nm in the presence of a DNA duplex and further to ~460 nm in the presence of a DNA quadruplex. In addition, the molar absorption coefficient decreased by ~15% in the presence of a DNA duplex and ~35% in the presence of a DNA quadruplex. These spectra changes indicate that compound 2 binds to duplexes and quadruplexes.

Fluorescence Analysis

Compound 2 was mixed with eleven DNAs and subjected to fluorescence analysis at $\lambda_{ex} \approx 430$ nm, using a Hitachi F4010 spectrofluorimeter with a 2 nm bandwidth in a 1-cm cell. Fluorescence analysis was also carried out for compound 4 or 6 in the presence of Hum24. The results showed that the fluorescence of each of compounds 2, 4, and 6 was weak. However, the fluorescence intensity unexpectedly increased in an order of magnitude in the presence of a DNA duplex and in two orders of magnitude in the presence of a DNA quadruplex. Further, the fluorescence peaks for a complex of compound 2 and a DNA duplex and a complex of compound 2 and a DNA quadruplex were at ~550 nm and ~575 nm, respectively.

These results suggest that compounds 2, 4, and 6 can be used to distinguish DNA duplexes from DNA quadruplexes. In addition, these compounds possess enhanced fluorescence upon binding to DNA quadruplexes and, therefore, can be used as a biomarker for DNA quadruplexes in electrophoresis.

CD Analysis:

Eight DNA quadruplexes and their complexes with compound 2 were subjected to CD analysis. CD spectra were averaged 10 scans on a Jasco J-715 spectropolarimeter with a 2 nm bandwidth. The scan speed was 50 nm/min and the step resolution was 0.2 nm.

No appreciable changes were detected in the CD spectra of DNA quadruplexes before and after compound 2 bound to them, suggesting that they were not distorted by binding with compound 2. The CD spectra also confirmed that anti-parallel quadruplexes dominate in Hum 12, Hum24, Oxy12, Oxy28, Tet12, and Apt.

Further, Hum24 and its complexes with compounds 2, 4, 6, and 8 were subjected to temperature-dependent CD analysis. The results showed that the melting temperature of Hum24 quadruplex increased in the presence of each of the four test compounds, indicating improved thermal stability.

Polyacrylamide Gel Eletrophoresis (PAGE)

The compound/DNA complexes described above were further analyzed by PAGE in 20% native gels in 10 mM Tris-HCl and 150 mM NaCl (pH 7.5). Gel electrophoresis was carried out in an electric field of 100 V/cm at 4° C. for 15 hours. DNA concentrations were determined by absorbencies at 260 nm and were adjusted to about 10 $\mu$M per unit structure. After photographing with UV shadowing, gels were post-stained in a solution containing 10 $\mu$M of a test compound, 10 mM Tris-HCl, and 150 mM NaCl (pH 7.5) at room temperature for 10 seconds. The gels were then rinsed by distilled water and photographed under 254 nm UV light using a digital camera.

Gels were post-stained with compound 2 after electrophoresis of AT, LD, GC, G10, LQ1, LQ2, LQ4, Tet12, Oxy12, Hum12, Apt, Oxy28, and Hum24 was complete. The results showed that that most DNAs exhibited fluorescence bands under 254 nm UV light. In particular, most DNAs migrated in the gel in a single band, but Tet12 and LQ4 migrated in two bands.

Pre-stained gels were used for selectivity assays. A 0.1 $\mu$M test compound solution was initially incubated with 10 $\mu$M of different DNA solutions for 10 minutes. Gel electrophoresis was then carried out in an electric field of 100 V/cm at 4° C. for 6 hours. All of the pre-stained gels were photographed under 254 nm UV light using a Bio-Rad imaging detector.

Gels pre-stained with compound 2 were used before running electrophoresis for AT, LD, GC, G10, LQ1, LQ2, LQ4, Tet12, Oxy12, Hum12, Apt, Oxy28, and Hum24. The results showed that the complexes of compound 2 and the quadruplexes of LQ2, LQ4, Oxy12, Oxy28, and Hum24 exhibited fluorescence bands under 254 nm UV light. Further, the complex of compound 2 and Tet12 quadruplex only exhibited a third fluorescence band in pre-stained gel electrophoresis, which was different from the two bands observed in post-stained gel electrophoresis. This third band is ascribed to be a linear tetramer of Tet12. On the other hand, no fluorescence bands were detected in the complexes of compound 2 and the quadruplexes of LD, AT, GC, G10, LQ1, Hum12, and Apt.

As mentioned above, Hum24, Oxy12, and Oxy28 contain at least one diagonal loop in their anti-parallel quadruplexes, and Apt, Tet12, and Hum12 contain no diagonal loop in their anti-parallel quadruplexes. Upon binding to compound 2, Hum24, Oxy12, and Oxy28 exhibited fluorescence bands, while Apt, Tet12, and Hum12 exhibited no fluorescence bands resulted from anti-parallel quadruplexes. This observation suggests that compound 2 can distinguish anti-parallel quadruplexes with diagonal loops from anti-parallel quadruplexes without diagonal loops.

In addition, fluorescence was exhibited by the complexes of compound 2 and the linear tetramers of LQ2 (containing $T_2$ tails) and LQ4 (containing $T_4$ tails), but not by those of compound 2 and the linear tetramers of LQ1 (containing T tails) and G10 (containing no T tails). These results suggest that compound 2 can also distinguish linear tetramers with different lengths of T tails.

To study the sensitivity of DNA detection using electrophoresis described above, a solution containing 0.1 $\mu$M of compound 2 was incubated with solutions containing 2.5 to 0.005 $\mu$M of Hum24. The mixtures were then subjected to electrophoresis. The sensitivity assay shows that 0.1 $\mu$M of a compound 2 solution can detect the presence of 0.01 $\mu$M of Hum24 quadruplex, indicating that compound 2 is a sensitive biomarker for detecting the presence of Hum24. Furthermore, the results also show that 0.1 $\mu$M of a compound 2 solution can detect the presence of 0.1 $\mu$M of LQ4 quadruplex, 0.1 $\mu$M of Oxy28 quadruplex, and a small amount of linear tetramer in 0.25 $\mu$M of Tet12 quadruplex.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of the formula:

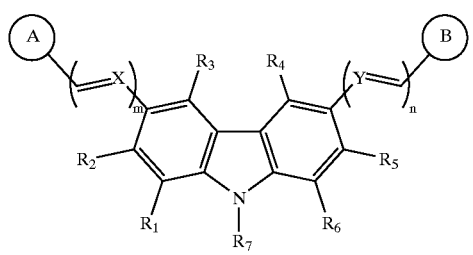

wherein each of rings A and B, independently, is heteroaryl containing at least one nitrogen atom;

each of X and Y, independently, is CH or N;

each of $R_1$–$R_6$, independently, is H, $C_1$–$C_8$ alkyl, $C_2$–$C_8$ alkenyl, $C_2$–$C_8$ alkynyl, $C_3$–$C_8$ cycloalkyl, $C_3$–$C_8$ heterocycloalkyl, aryl, heteroaryl, OH, $C_1$–$C_6$ alkoxy, aryloxy, heteroaryloxy, $NH_2$, $C_1$–$C_6$ alkylamino, $C_1$–$C_{12}$ dialkylamino, arylamino, diarylamino, or halogen;

$R_7$ is H; and each of m and n, independently, is 1, 2, or 3.

2. The compound of claim 1, wherein each of rings A and B is heteroaryl containing one or two nitrogen atoms.

3. The compound of claim 2, wherein each of m and n is 1.

4. The compound of claim 3, wherein each of $R_1$–$R_7$ is H.

5. The compound of claim 4, wherein each of X and Y is CH.

6. The compound of claim 5, wherein the compound is

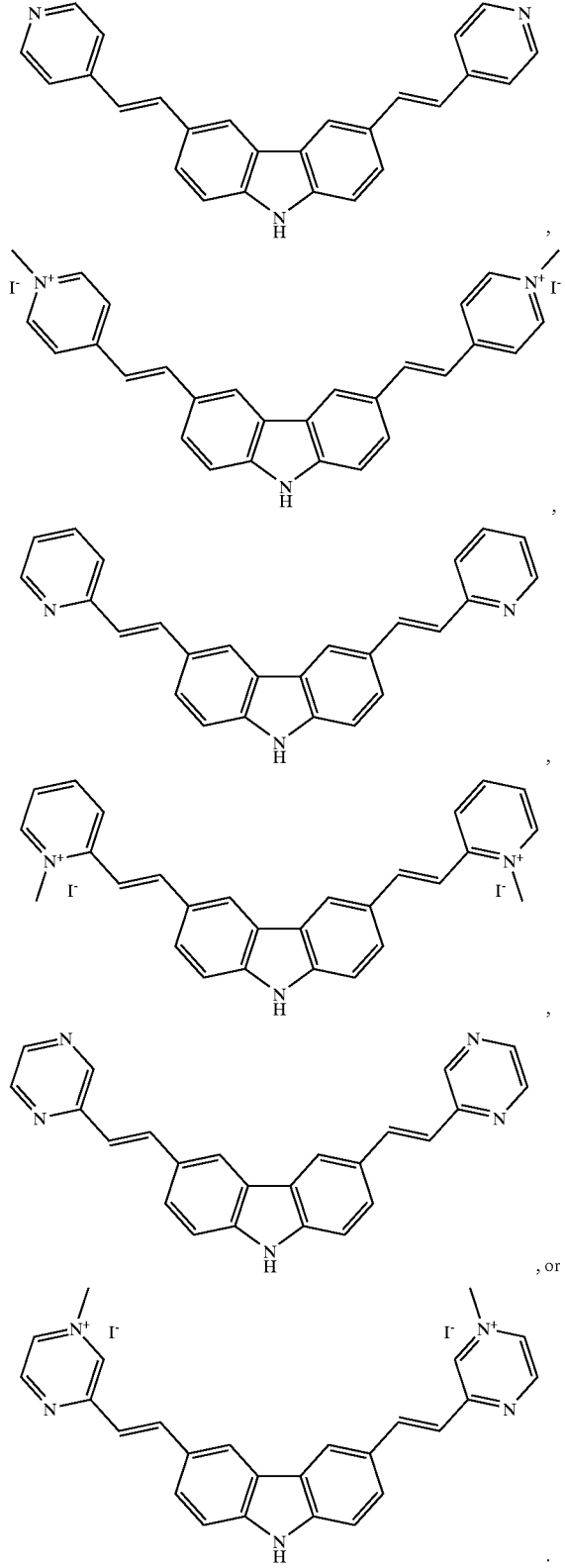

7. The compound of claim 4, wherein each of X and Y is N.

8. The compound of claim 7, wherein the compound is

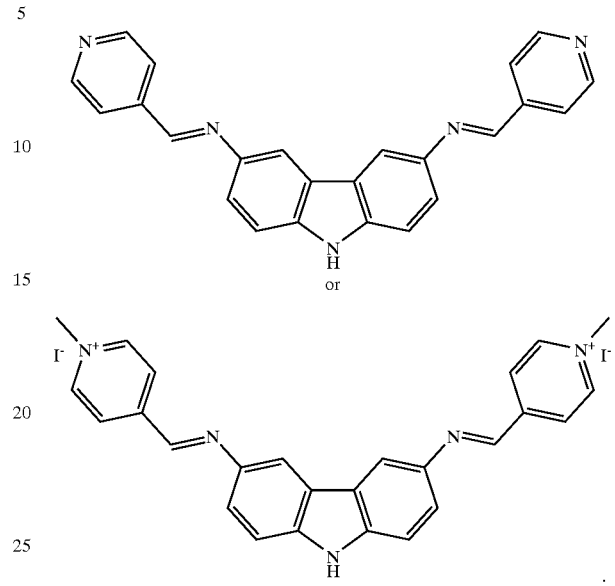

9. The compound of claim 1, wherein each of m and n is 1.

10. The compound of claim 9, wherein each of $R_1$–$R_7$ is H.

11. The compound of claim 1, wherein each of $R_1$–$R_7$ is H.

12. A method for stabilizing a G-quadruplex of a telomere, comprising contacting a telomere with a compound of the formula:

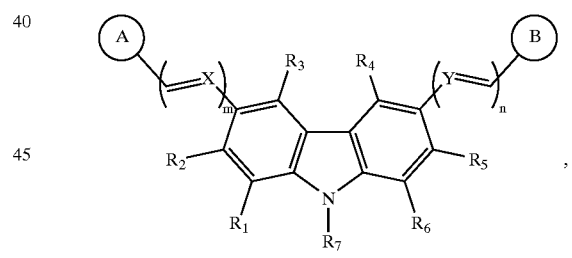

wherein
  each of rings A and B, independently, is heteroaryl containing at least one nitrogen atom;
  each of X and Y, independently, is CH or N;
  each of $R_1$–$R_6$ independently, is H, $C_1$–$C_8$ alkyl, $C_2$–$C_8$ alkenyl, $C_2$–$C_8$ alkynyl, $C_3$–$C_8$ cycloalkyl, $C_3$–$C_8$ heterocycloalkyl, aryl, heteroaryl, OH, $C_1$–$C_6$ alkoxy, aryloxy, heteroaryloxy, $NH_2$, $C_1$–$C_6$ alkylamino, $C_1$–$C_{12}$ dialkylamino, arylamino, diarylamino, or halogen;
  $R_7$ is H, $C_1$–$C_8$ alkyl, $C_2$–$C_8$ alkenyl, $C_2$–$C_8$ alkynyl, $C_3$–$C_8$ cycloalkyl, $C_3$–$C_8$ heterocycloalkyl, aryl, heteroaryl; and
  each of m and n, independently, is 1, 2, or 3.

13. The method of claim 12, wherein each of rings A and B is heteroaryl containing one or two nitrogen atoms.

14. The method of claim 13, wherein each of m and n is 1.

15. The method of claim 14, wherein each of $R_1$–$R_7$ is H.
16. The method of claim 15, wherein each of X and Y is CH.
17. The method of claim 16, wherein the compound is
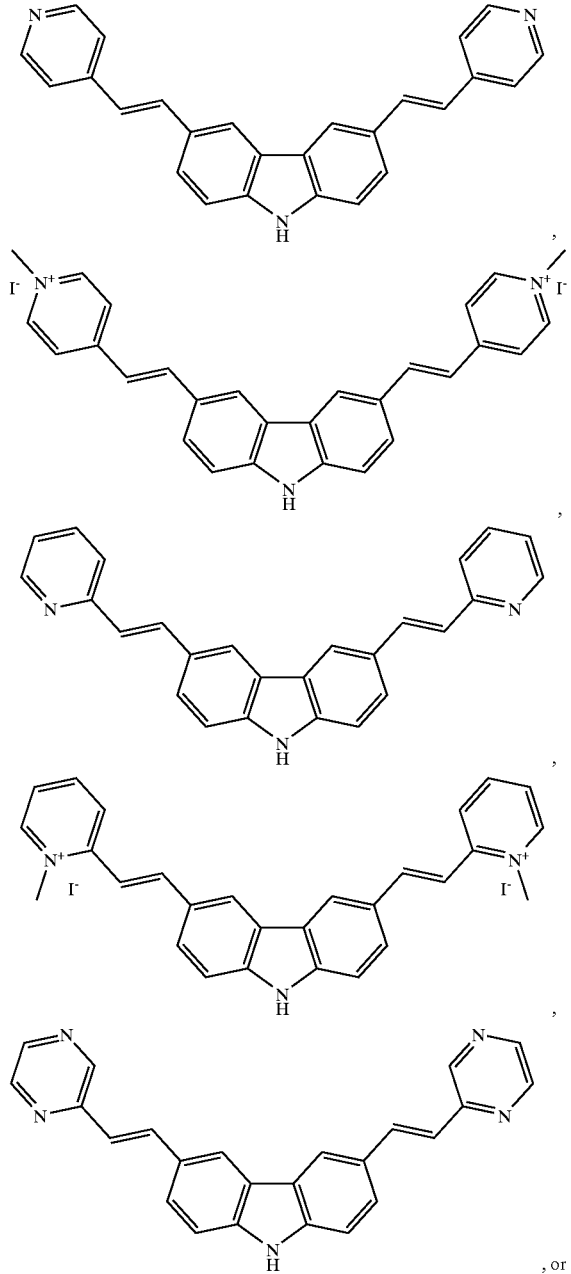
,
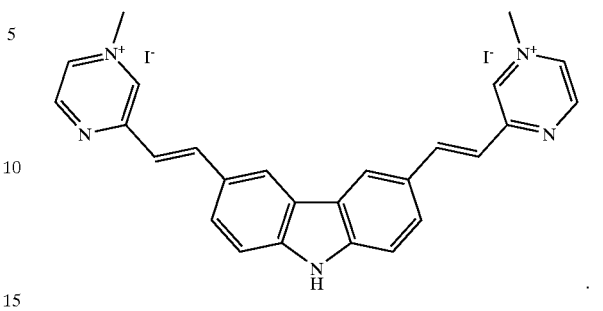
18. The method of claim 15, wherein each of X and Y is N.
19. The method of claim 18, wherein the compound is
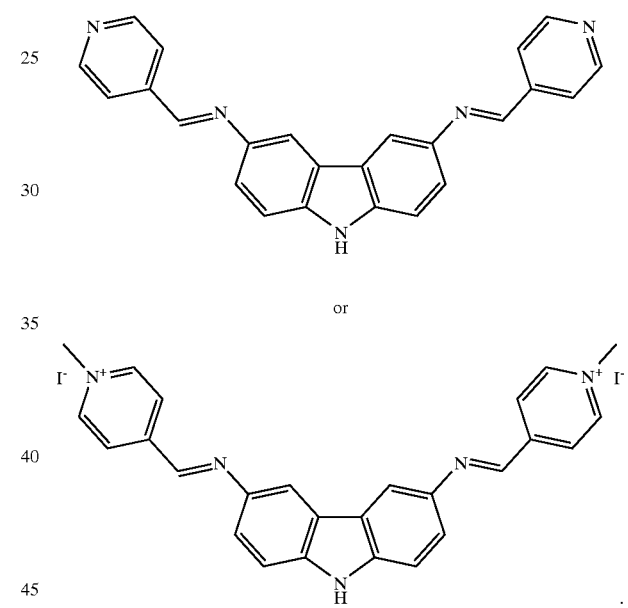
.
20. The method of claim 12, wherein each of m and n is 1.
21. The method of claim 20, wherein each of $R_1$–$R_7$ is H.
22. The method of claim 12, wherein each of $R_1$–$R_7$ is H.
* * * * *

SEQUENCE LISTING

<160> NUMBER OF SEQ ID NOS: 13

<210> SEQ ID NO 1
<211> LENGTH: 12
<212> TYPE: DNA
<213> ORGANISM: Artificial Sequence
<220> FEATURE:
<223> OTHER INFORMATION: Synthetically generated  oligonucleotide

<400> SEQUENCE: 1
atatatatat at                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetically generated  oligonucleotide

<400> SEQUENCE: 2
gcgcaattgc gc                                                          12

<210> SEQ ID NO 3

```
<211> LENGTH: 12
<212> TYPE: DNA
<213> ORGANISM: Artificial Sequence
<220> FEATURE:
<223> OTHER INFORMATION: Synthetically generated  oligonucleotide

<400> SEQUENCE: 3
gcgcgcgcgc gc                                                          12

<210> SEQ ID NO 4
<211> LENGTH: 10
<212> TYPE: DNA
<213> ORGANISM: Artificial Sequence
<220> FEATURE:
<223> OTHER INFORMATION: Synthetically generated  oligonucleotide

<400> SEQUENCE: 4
gggggggggg                                                             10

<210> SEQ ID NO 5
<211> LENGTH: 6
<212> TYPE: DNA
<213> ORGANISM: Artificial Sequence
<220> FEATURE:
<223> OTHER INFORMATION: Synthetically generated  oligonucleotide

<400> SEQUENCE: 5 tggggt                                                                  6

<210> SEQ ID NO 6
<211> LENGTH: 8
<212> TYPE: DNA
<213> ORGANISM: Artificial Sequence
<220> FEATURE:
<223> OTHER INFORMATION: Synthetically generated oligonucleotide

<400> SEQUENCE: 6 ttggggtt                                                                8

<210> SEQ ID NO 7
<211> LENGTH: 8
<212> TYPE: DNA
<213> ORGANISM: Artificial Sequence
<220> FEATURE:
<223> OTHER INFORMATION: Synthetically generated oligonucleotide

<400> SEQUENCE: 7 ttttgggg                                                                8

<210> SEQ ID NO 8
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 8
ttggggttgg gg                                                          12

<210> SEQ ID NO 9
<211> LENGTH: 15
<212> TYPE: DNA
```

```
-continued

<213> ORGANISM: Artificial Sequence
<220> FEATURE:
<223> OTHER INFORMATION: Synthetically generated oligonucleotide

<400> SEQUENCE: 9
ggttggtgtg gttgg                                                     15

<210> SEQ ID NO 10
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 10
ggggttttgg gg                                                        12

<210> SEQ ID NO 11
<211> LENGTH: 28
<212> TYPE: DNA
<213> ORGANISM: Artificial Sequence
<220> FEATURE:
<223> OTHER INFORMATION: Synthetically generated oligonucleotide

<400> SEQUENCE: 11
ggggttttgg ggttttgggg ttttgggg                                       28

<210> SEQ ID NO 12
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 12
ttagggttag gg                                                        12

<210> SEQ ID NO 13
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 13
ttagggttag ggttagggtt aggg                                           24
```